United States Patent [19]

Maurer et al.

[11] Patent Number: 4,632,991
[45] Date of Patent: Dec. 30, 1986

[54] PROCESS FOR PRODUCTION OF ZINC 2-MERCAPTOPYRIDINE-N-OXIDE

[75] Inventors: Manfred Maurer, Kirchheim; Winifried Orth, Hassloch; Werner Fickert, Mannheim, all of Fed. Rep. of Germany

[73] Assignee: Rutgerswerke AG, Fed. Rep. of Germany

[21] Appl. No.: 695,410

[22] Filed: Jan. 25, 1985

Related U.S. Application Data

[63] Continuation of Ser. No. 395,660, Jul. 6, 1982, abandoned.

[30] Foreign Application Priority Data

Jul. 15, 1981 [DE] Fed. Rep. of Germany ....... 3127863

[51] Int. Cl.$^4$ ........................................... C07D 213/89
[52] U.S. Cl. ........................................... 546/6
[58] Field of Search ........................................... 546/6

[56] References Cited

U.S. PATENT DOCUMENTS 2,809,971 10/1957 Bernstein ................................. 546/2
3,700,676 10/1972 Damico ................................. 424/70
3,785,985 1/1974 Grand ................................. 546/2
4,323,683 4/1982 Bolich, Jr. ................................. 546/2
4,533,736 8/1985 Trotz et al. ................................. 546/6

OTHER PUBLICATIONS

Davis et al., Chem. Abs. 100, 39616p, (1983).
Jerchel et al., Chem. Abs. 49, 11579(g), 1954.
McCutcheon's Detergents and Emulsifiers, 1975 Annual, pp. 18, 27, 45, 55, 57, 78, 82, 83, 91, 133.
Kirk–Othmer, Encyclopedia of Chem. Technology, 3rd Edition, vol. 8, pp. 912–915.

Primary Examiner—Mark L. Berch
Attorney, Agent, or Firm—Bierman, Peroff & Muserlian

[57] ABSTRACT

The present invention relates to a process for the preparation of zinc 2-mercaptopyridine-N-oxide in a readily filterable, washable and easily suspendable form which comprises reacting an aqueous solution of an alkali metal salt of 2-mercaptopyridine-N-oxide with an aqueous solution of a water soluble zinc salt at a temperature of 35° to 100° C. in the presence of an at least partially water soluble organic solvent to form a precipitate of zinc 2-mercaptopyridine-N-oxide, recovering the said crystals and optionally comminuting the crystals.

7 Claims, No Drawings

PROCESS FOR PRODUCTION OF ZINC 2-MERCAPTOPYRIDINE-N-OXIDE

PRIOR APPLICATION

This application is a continuation of copending U.S. patent application Ser. No. 395,660 filed July 6, 1982, now abandoned.

BACKGROUND OF THE INVENTION

The invention relates to a process for the production of the zinc salt of 2-mercaptopyridine-N-oxide in a form in which the product filters easily, washes easily and will form stable suspensions.

Under the name Zinkpyrion, the zinc salt of 2-mercaptopyridine-N-oxide is a well known commercial product. The compound has a broad spectrum activity against fungi and yeasts and its activity is independent of pH. The product is used in cosmetics, especially as and anti-dandruff agent in the manufacture of shampoo compositions and such compositions are described in copending U.S. patent application Ser. No. 360,555 filed Mar. 22, 1982, ABN which is incorporated herein by reference. In the industrial sector, suspensions of this zinc salt are used in those areas where protection from attack by the storage preservation of dispersion paints and laquets, bacteria, fungi and yeasts is desirable, e.g. for the storage preservation of dispersion and paints laquers, acrylates or styrene-butadiene polymers, etc.

The preparation of the zinc salt of 2-mercaptopyridine N-oxide is known and it may be obtained by reaction of aqueous zinc salt solutions (e.g. zinc chloride, zinc sulfate) with aqueous solutions of the sodium salt of 2-mercaptopyridine-N-oxide at temperatures between 20° and 80° C., in particular at 50° to 60° C. The preparation of aqueous sodium-2-mercaptopyridine-N-oxide solutions has been described in the literature (U.S. Pat. No. 3,159,640). The zinc 2-mercaptopyridine-N-oxide thus prepared has an average grain size of 2 to 3 microns and consists mainly of cubic and octahedral crystals which are in part agglomerated. Such finecrystalline precipitates are very difficult to isolate by filtration, which is very time-consuming and elution of extraneous ions (e.g. $Na^+Cl^-$) is laborious and also requires much time. Moreover, the resulting pastes still contain up to 45-48% water.

The product is marketed as an aqueous, whitecreamy suspension and in an older application, copending, commonly assigned U.S. patent application Ser. No. 360,550 filed Apr. 6, 1982, ABN the suspension is obtained by the action of shearing forces on water-containing zinc salt of 2-mercaptopyridine-N-oxide in the presence of anionic surfactants (suspension with 48% active substance content) or non-ionic water-soluble cellulose derivatives (suspension with 40% active substance content). Despite the small crystal size, the stability of such suspensions is at most 2.5 to 3 months.

Because of these disadvantages, the urgent need and the problem to be solved was to prepare the zinc salt of 2-mercaptopyridine-N-oxide in a form easy to filter and yet can be incorporated into a stable suspension, or respectively to find a manufacturing process in which the zinc salt is obtained in this form.

OBJECTS OF THE INVENTION

It is the object of the present invention to provide an improved method for the production of zinc 2-mercaptopyridine-N-oxide.

It is another object of the present invention to produce zinc 2-mercaptopyridine-N-oxide with improved properties which include filterability, washability and great stability when in the form of a suspension.

Another object of the present invention is to react an aqueous solution of sodium 2-mercaptopyridine-N-oxide with an aqueous solution of a water soluble zinc salt at a temperature in the range of 35° to 100° C. in the presence of a water soluble or partially water soluble organic solvent.

It is an additional object of the invention to provide novel, more stable aqueous suspensions of zinc 2-mercaptopyridine-N-oxide.

These and other objects of the invention will become more apparent from the following detailed description thereof.

DESCRIPTION OF THE INVENTION

The process of the invention is for the preparation of the zinc salt of 2-mercaptopyridine-N-oxide in a readily filterable, washable and easily suspendable form comprises reacting an aqueous solution of an alkali metal salt of 2-mercaptopyridine-N-oxide with an aqueous solution of a water soluble zinc salt at a temperature of 35° to 100° C. in the presence of an at least partially water soluble organic solvent to form a precipitate of crystalline zinc 2-mercaptopyridine-N-oxide, recovering the said crystals and optionally comminuting the said crystals.

It is evident from theoretical considerations that the filterability of the product can be improved by increasing the size of the crystals formed during precipitation or respectively by preventing the individual crystals from agglomerating. All attempts at achieving this with the usual methods such as raising the precipitation temperature, fractional precipitation, or stronger agitation, have not led to the desired result.

It has now been found, surprisingly, that the addition of wholly or partly water-soluble organic solvents, in which the zinc salt of 2-mercaptopyridine-N-oxide are themselves only slightly soluble, to solutions of the sodium salt of 2-mercaptopyridine-N-oxide while reacting at above 50° C. with water-soluble zinc salts (e.g. zinc chloride or zinc sulfate) gives a crystalline zinc 2-mercaptopyridine N-oxide with larger crystal diameters than is usually obtained. Suitable organic solvents are: lower alkanols of 1 to 5 carbon atoms such as; methanol, ethanol, isopropanol, t-butanol, etc.; polyvalent alcohols, e.g. ethylene glycol, propylene glycol, glycerol, etc.; amides and substituted amides, e.g. formamide, N, N-dimethyl formamide, N,N-diethyl acetamide, hexamethyl phosphoric acid triamide, N-formyl pyrrolidine or N-formyl piperidine; ketones; acetronitrile, ethers, e.g. tetrahydrofuran; dioxane, ethylene glycol dimethyl ether and ethylene glycol e.g. acetone, methylethyl ketone; nitriles, e.g. diethyl ether; substances with mixed alcohol-ether functions, e.g. ethylene glycol monomethyl ether, ethylene glycol monoethyl ether; dimethyl sulfoxide; and mixtures of these solvents.

Especially advantageous are those solvents whose boiling points are below that of water and which can be separated therefrom by distillation in a simple manner, such as methanol, ethanol, isopanol, acetone and ethylene glycol dimethyl ether. The recovered solvents can be reused (taking their water content into consideration), thus making the method especially economical.

The reaction temperatures lie in the range of 35° to 100° C., preferably between 60° and 70° C., with the crystal size, i.e. the average length of the longitudinal axes of the crystals, of the zinc 2-mercaptopyridine-N-oxide increasing at higher temperatures.

The resulting crystal size also depends on the amount of solvent added. Starting with solutions containing about 17% by weight of sodium 2-mercaptopyridine-N-oxide solutions, it suffices to add 13% by weight of at least partially water soluble solvent, based on the weight of the sodium salt solution, to obtain crystals of 5 to 7 microns. Increasing the amount of solvent added leads to increasingly larger crystals. When adding 50% by weight of the said solvent, one can obtain crystals some of which are larger than ½ mm. i.e. 500 microns. The solvent can all be added to the aqueous solution of sodium 2-mercaptopyridine-N-oxide or it can be added partly to the precipitant solution (e.g. aqueous acid zinc chloride solution). In the case of ethylene glycol dimethyl ether (13%, based on the sodium-2-mercaptopyridine N-oxide solution), one obtains, with a ratio of ⅔ of the ether in the sodium salt solution and ⅓ in the zinc salt precipitation solution, especially homogeneous zinc 2-mercaptopyridine-N-oxide crystals with a crystal size of 5 to 6 microns.

It is, therefore, a further unexpected advantage of the process of the invention that besides great homogeneity of the crystals, the crystal size of the zinc salt can be varied almost at will in the range of from 5 to 500 microns by skillful combination of reaction temperature and solvent quantity.

Surprisingly, the resulting crystals are not agglomerated and therefor, the crystal paste is easy to filter and wash, i.e. an additional advantage results in the clearly easier and faster isolation of the zinc salt of 2-mercaptopyridine-N-oxide produced by the new method. For a grain size of 5 to 7 microns, the time requirement for the filtration (including washing with water) is about one third in comparison with the known method. For a grain size of about 100 microns, it is only about one sixth of the time of the known method. Moreover, the water content is decreased with the process of the invention to an average of 20 to 25% as against 45% in the known method which gives essential advantages in the handling and a considerable saving of costs in the shipping or drying of the paste.

When preparing anionic or non-ionic suspensions similar to those of U.S. patent application Ser. No. 360,555, ABN the action of shearing forces on corresponding formulations containing fine crystalline zinc salt of 2-mercaptopyridine-N-oxide produced by the method of the invention, one obtains, surprisingly, especially stable products with a shelf life of more than 5 to 6 months without too much sediment settling out. This advantage is entirely unexpected, for on the basis of the greater grain size of the crystals as compared with those precipitated from purely aqueous solution rather the opposite was to be expected.

An additional improvement of the stability of suspensions containing the zinc salts produced by the method of the invention can be achieved by precipitating the said zinc salt crystals in the size of 10 to 200 microns, preferably 50 to 100 microns, comminuting them mechanically to a size of 2 to 8 microns, and further processing these crystals to form a suspension which is much stabler than a suspension of zinc 2-mercaptopyridine-N-oxide crystals precipitated originally in a size range of 2 to 8 microns, i.e. such a suspension is much more stable and the active substance settles out of suspension much less. It is clear that the stability of the suspensions is greater, the more the crystals have been comminuted, i.e. in principle crystals as small as possible are desireable. The upper crystal size should be about 8 microns and with modern grinding equipment such as pearl, sand or vibratory mills, it is possible to comminute the zinc salts to about 0.5 micron. From these crystal fragments, to which no specific crystal structure can be assigned but which have a very large specific surface area, extremely stable suspensions can be produced.

The novel stable suspensions of the invention are aqueous suspensions of the zinc salt of 2-mercaptopyridine-N-oxide prepared by the process of the invention and containing at least one non-ionic, water-soluble cellulose derivative as the suspending agent.

Examples of suitable water-soluble cellulose derivatives are the cellulose ethers such as alkyl and hydroxyalkyl ethers of cellulose of 1 to 6 alkyl carbon atoms and mixed ethers thereof. Specific ethers are methycellulose, ethylcellulose, hydroxyethylcellulose, hydroxpropycellulose, methylhydroxyethylcellulose and methylhydroxypropylcellulose. The cellulose ethers are commercial products which have been used commercially as thickening agents and in wall paper glues.

It is most surprising that thin suspensions can be obtained from an aqueous pasty slurry containing 35 to 70% by weight of water and small amounts of at least one water-soluble cellulose derivative. The suspensions preferably contain 0.1 to 2.0%, most preferably 0.5 to 0.6%, by weight based on the weight of the zinc salt in the suspension. Larger amounts of the cellulose derivative may be used but the resulting suspension is too thick which makes the handling of the suspension difficult.

The cellulose derivative may be added directly to an intensely stirred aqueous slurry of the zinc salt of 2-mercaptopyridine-N-oxide until the cellulose derivative is dissolved. Preferably, however, the water-soluble cellulose derivative is dissolved in water first and the resulting solution is mixed with strong shear forces with the aqueous slurry of the said zinc salt.

To obtain a suspension which is stable for at least 3 months, the shear forces used to form the suspension should be strong, on the order of 10,000 rpm for 15 to 20 minutes in an apparatus such as the Ultraturrax type. The preferred suspensions contain about 40% by weight of the said zinc salt for the best storage stability and visco-elastic characteristics although larger or lower concentrations of the zinc salt may be used.

In the following examples there are described several preferred embodiments to illustrate the invention. However, it should be understood that the invention is not intended to be limited to the specific embodiments.

EXAMPLES

EXAMPLE I 3360 g of a 17.7 wt. % solution of the sodium salt of 2-mercaptopyridine-N-oxide and 301 g of ethylene glycol dimethyl ether were heated to 60° C. There was added dropwise a mixture of 444 g of 65% zinc chloride solution and 118 g of concentrated hydrochloric acid and 134 g of ethylene glycol dimethyl ether. The mixture was cooled to room temperature, suction-filtered and washed with 1500 ml of iron-free water. It was thoroughly filtered.

The yield was 848 g (containing 25% water).
The dry yield was 635 g (100% of theory).
The color was white to faintly beige.
The crystal size was 5 to 7 microns.
The filtering and washing time was 20 min.
The solvent addition was 13% based on the weight of the sodium salt solution.

COMPARISON TEST

The procedure was indicated in Example 1, the ethylene glycol dimethyl ether additions were omitted.
The yield was 1198 g (containing 47% water).
The dry yield was 635 g (100% of theory).
The color was white to beige.
The crystal size was 2 to 3 microns.
The filtering and washing time was 1 hour.

EXAMPLE 2

The procedure was as described in Example 1, but at the reflux temperature of the added ethylene glycol dimethyl ether. There prevailed in the sump a temperature of 90° to 93° C.
The yield was 747 g (containing 15% water).
The dry yield was 636 g (100% of theory).
The color was beige.
The crystal size was 10 to 13 microns.
The filtering and washing time was 12 to 15 minutes.

EXAMPLE 3

3360 g of a 17.1 wt. % solution of sodium 2-mercaptopyridine-N-oxide and 1586 g of N, N-dimethyl formamide or N, N-diethyl formamide or N, N-dimethyl acetamide were heated to 70° to 80° C. while stirring. Then there was added dropwise a mixture of 444 g of 65% zinc chloride solution and 118 g of concentrated hydrochloric acid. The mixture was cooled to room temperature, suction filtered and washed with 1500 ml of iron free water. It was thoroughly filtered.
The yield was 686.5 g (containing 7.5% water).
The dry yield was 635 g (100% of theory).
The color was beige.
The crystal size was around 500 microns.
The filtering and washing time was barely 10 minutes.
The solvent addition was 47%, based on the weight of the sodium salt solution.

EXAMPLE 4

The procedure was as described in Example 1, but using methanol, ethanol, isopropanol, t-butanol, acetone, acetonitrile, dioxane and tetrahdrofuran instead of ethylene glycol dimethyl ether.
The yield was 900 g (containing approx. 30% water).
The dry yield was 636 g (100%).
The color was white to beige.
The crystal size was 3 to 6 microns.
The filtering and washing time was about 30 to 35 minutes.

EXAMPLE 5

The procedure was as described in Example 2, but using ethylene glycol momomethyl ether, ethylene glycol diethyl ether or formamide instead of ethylene glycol dimethyl ether.
The yield was approximately 980 g (containing approx. 33% water).
The dry yield was 635 g (100% of theory).
The color was beige.
The crystal size was 3 to 5 microns.
The filtering and washing time was 35 to 40 minutes.

EXAMPLE 6

3360 g of a 17.1 wt. % solution of sodium 3-mercaptopyridine-N-oxide and 512 g of hexamethyl phosphoric acid triamide were heated to 70° to 80° C. To this was added dropwise a mixture of 444 g of 65% zinc chloride solution and 118 g of concentrated hydrochloric acid and 176 g of hexamethyl phosphoric acid triamide, cooling to room temperature, suction filtering, and washing with 1500 ml of iron-free water. It was thoroughly filtered.
The yield was 722 g (containing 12% water).
The dry yield was 635 g (100% of theory).
The color was white to beige.
The crystal size was about 100 microns.
The solvent addition was 20% based on weight of sodium salt solution.
The filtering and washing time was about 10 to 15 minutes.

EXAMPLE 7

The procedure was according to Example 1, but using N-methyl pyrrolidine, N-methyl piperdine, N-formyl pyrrolidine or dimethyl sulfoxide instead of ethylene glycol dimethyl ether.
The yield was 882 g (containing approx. 28% water).
The dry yield was 635 g (100% of theory).
The color was white to faintly beige.
The crystal size was 4 to 6 microns.
The filtering and washing time was about 20 minutes.

EXAMPLE 8

3360 g of a 17.1% solution of sodium 2-mercaptopyridine-N-oxide and 541 g methyl ethyl ketone were heated to 70° C. while stirring. To this was added dropwise a mixture of 444 g of 65% zinc chloride solution and 118 g of concentrated hydrochloric acid. The mixture was cooled to room temperature, suction filtered and washed with iron-free water. The precipitate was thoroughly filtered.
The yield was 794 g (containing 20% water).
The dry yield was 635 g (100% of theory).
The color was white to beige.
The crystal size was 6 to 10 microns.
The filtering and washing time was about 20 minutes.
The solvent addition was 16% based on the weight of the sodium salt solution.

EXAMPLE 9

Zinc-2-mercaptopyridine-N-oxide was suspended in water in a concentration of 48 wt. % with a small addition of an anionic surfactant under the application of shearing forces. The following forms of the zinc-2-mercaptopyridine-N-oxide were used: (a) conventional crystal form, precipitated without addition of solvent; size 2 to 3 microns (analogous to the comparison example which followed example 1.) (b) conventional crystal form, zinc salt precipitated without addition of solvent in a size of 2 to 3 microns and then comminuted to a size of 0.5 to 2 microns. (c) zinc salt precipitated per invention with addition of solvent (analogous to Example 1) in a size of 5 to 7 microns. (d) Zinc salt precipitated per invention with addition of solvent (analogous to Example 6) in a size of about 100 microns and then comminuted to a size of 5 to 8 microns. (e) Zinc salt precipitated per invention with addition of solvent (analogous to Example 6) in a size of about 100 micron and then comminuted to a size of 0.5 to 2 microns.

The suspensions were filled into a mixing cylinder to a height of 30 cm and kept undisturbed at room temperature for 6 months. Thereafter the following settling behavior was observed:

(a) Clear, supernatant liquid column of a height of 21 mm heavy sediment which can no longer be stirred up.

(b) Clear, supernatant liquid of a height of 14 mm, pronounced sediment which was difficult to stir up.

(c) Clear, supernatant liquid of a height of 11 mm, slight sediment, can be stirred up easily.

(d) Slightly cloudy supernatant liquid of a height of 5 mm no sediment.

(e) Cloudy supernatant liquid of a height of 2 mm, no sediment.

EXAMPLE 10

Hydroxethyl cellulose (2.4 g) is dissolved in 530 ml water with intense agitation. Into this solution was introduced while stirring, 470 g of a zinc-2-mercaptopyridine-N-oxide prepared according to Example 2 (water content 15 wt %). The suspension thus prepared is subjected to the shearing forces of a modern mill equipment, the zinc salt crystals being comminuted to 0.5 to 2 microns. One obtains an approximately 40% suspension, the stability of which is so great that in the settling test according to Example 9 almost no settling is observed.

The preceding specific embodiments are illustrative of the practice of the invention. It is to be understood, however, that other expendients known to those skilled in the art may be employed without departing from the spirit of the invention or the scope of the appended claims.

We claim:

1. A process for the preparation of the zinc salt of 2-mercaptopyridine-N-oxide in a readily filterable, washable and easily suspendable form comprising reacting in the absence of a surfactant an aqueous solution of an alkali metal salt of 2-mercaptopyridine-N-oxide and an aqueous solution of a water soluble zinc salt at a temperature in the range of 35° to 100° C. in the presence of 10 to 50% by weight of an at least partially water soluble organic solvent based on the weight of the sodium 2-mercaptopyridine-N-oxide solution to form a precipitate of crystalline zinc-2-mercaptopyridine-N-oxide, recovering said crystals and optionally comminuting the crystals.

2. A process of claim 1 wherein the at least partially water soluble organic solvent is selected from the group consisting of secondary of tertiary alkanols, polyvalent alcohols, amides and substituted amides, teritary amines, ketones, nitriles, dimethyl sulfoxide, ether, substances with mixed alcohol/ether function and mixtures of the said solvents.

3. A process of claim 1, wherein the precipitation reaction is carried out at a temperature of about 60° to 70° C.

4. A process of claim 1 wherein the precipitation is carried out at a temperature of about 60° to 80° C., with a solvent addition of 20 to 40% by weight based on the weight of sodium 2-mercaptopyridine-N-oxide solution, to obtain 10 to 500 micron crystals of the zinc 2-mercaptopyridine-N-oxide and mechanically comminuting the crystals after isolation.

5. A process of claim 4, wherein the crystals of the zinc 2-mercaptopyridine-N-oxide are comminuted to an average size of 2 to 8 microns.

6. A process of claim 4, wherein the crystals of the zinc 2-mercaptopyridine-N-oxide are comminuted to an average size of 0.5 to 2 microns.

7. A process of claim 1 wherein the solvents are added in quantities of 10 to 15 % by weight based on the weight of sodium-2-mercaptopyridine-N-oxide solution.

* * * * *